US008669393B2

(12) United States Patent
Boussie et al.

(10) Patent No.: US 8,669,393 B2
(45) Date of Patent: Mar. 11, 2014

(54) ADIPIC ACID COMPOSITIONS

(75) Inventors: Thomas R. Boussie, Menlo Park, CA (US); Eric L. Dias, Belmont, CA (US); Zachary M. Fresco, Redwood City, CA (US); Vincent J. Murphy, San Jose, CA (US); James Shoemaker, Gilroy, CA (US); Raymond Archer, Sunnyvale, CA (US); Hong Jiang, Palo Alto, CA (US)

(73) Assignee: Rennovia, Inc., Menlo Park, CA (US)

(*) Notice: Subject to any disclaimer, the term of this patent is extended or adjusted under 35 U.S.C. 154(b) by 422 days.

(21) Appl. No.: 12/966,783

(22) Filed: Dec. 13, 2010

(65) Prior Publication Data
US 2011/0218318 A1    Sep. 8, 2011

Related U.S. Application Data

(63) Continuation-in-part of application No. 12/814,188, filed on Jun. 11, 2010.

(60) Provisional application No. 61/311,190, filed on Mar. 5, 2010.

(51) Int. Cl.
C07C 69/74    (2006.01)

(52) U.S. Cl.
USPC ............................................................ 560/1

(58) Field of Classification Search
USPC ........... 528/302; 540/485; 435/135; 558/311; 568/864; 549/292; 562/590
See application file for complete search history.

(56) References Cited

U.S. PATENT DOCUMENTS

| | | | |
|---|---|---|---|
| 2,472,168 A | 6/1949 | Mehltretter et al. |
| 2,750,394 A | 6/1956 | Peniston |
| 2,851,468 A | 9/1958 | Snyder |
| 2,917,520 A | 12/1959 | Cope |
| 2,929,823 A | 3/1960 | Garber et al. |
| 3,070,633 A | 12/1962 | Utne et al. |
| 3,083,236 A | 3/1963 | Utne et al. |
| 3,118,912 A | 1/1964 | Smith |
| 3,189,651 A | 6/1965 | Garber et al. |
| 3,225,066 A | 12/1965 | Baak |
| 3,326,944 A | 6/1967 | Baak |
| 3,483,228 A | 12/1969 | Garber et al. |
| 3,607,922 A | 9/1971 | Acres et al. |
| 3,671,566 A | 6/1972 | Decker et al. |
| 3,761,579 A | 9/1973 | Curtis, Jr. et al. |
| 3,860,626 A | 1/1975 | Putnin et al. |
| 3,873,614 A | 3/1975 | Lamberti et al. |
| 3,896,056 A | 7/1975 | Benjamin et al. |
| 3,917,707 A | 11/1975 | Williams et al. |
| 4,067,900 A | 1/1978 | Intilli |
| 4,078,139 A | 3/1978 | Barton et al. |
| 4,302,432 A | 11/1981 | Polichnowski |
| 4,337,202 A | 6/1982 | Hearon et al. |

(Continued)

FOREIGN PATENT DOCUMENTS

| | | |
|---|---|---|
| CA | 2097812 A1 | 6/1992 |
| CN | 101486639 | 7/2009 |

(Continued)

OTHER PUBLICATIONS

Kouremenos et al., Metabolic profiling of infant urine using comprehensive two-dimensional gas chromatography: Application to the diagnosis of organic acidurias and biomarker discovery, Journal of Chromatography A, 1217 (2010) Available online Oct. 20, 2009, pp. 104-111.*

(Continued)

Primary Examiner — Wu-Cheng Winston Shen
Assistant Examiner — Blaine G Doletski
(74) Attorney, Agent, or Firm — Senniger Powers LLP

(57) ABSTRACT

Disclosed are compositions of matter comprising an adipic acid product of formula (1)

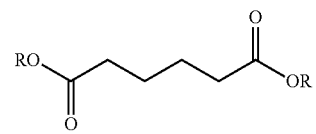

wherein R is independently a salt-forming ion, hydrogen, hydrocarbyl, or substituted hydrocarbyl, and
at least one constituent selected from the group consisting of formula (2)

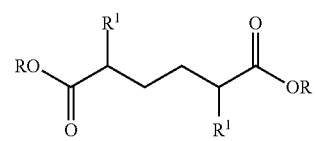

wherein R is as defined above and each of R1 is, independently, H, OH, acyloxy or substituted acyloxy provided, however, that at least one of R1 is OH, and formula (3)

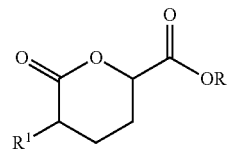

wherein R is as above defined and R1 is OH, acyloxy or substituted acyloxy. Also disclosed are compositions of matter comprising at least about 99 wt % adipic acid and least two constituents selected from the group consisting of formula (2) and formula (3), above.

18 Claims, No Drawings

(56) References Cited

U.S. PATENT DOCUMENTS

| | | |
|---|---|---|
| 4,339,387 A | 7/1982 | Fleche et al. |
| 4,363,815 A | 12/1982 | Yu et al. |
| 4,400,468 A | 8/1983 | Faber |
| 4,401,823 A | 8/1983 | Arena |
| 4,439,551 A | 3/1984 | Yeakey et al. |
| 4,533,743 A | 8/1985 | Medeiros et al. |
| 4,590,283 A | 5/1986 | Gaset et al. |
| 4,605,790 A | 8/1986 | Wojtkowski |
| 4,722,997 A | 2/1988 | Roerdink et al. |
| 4,740,605 A | 4/1988 | Rapp |
| 4,767,856 A | 8/1988 | Dockner et al. |
| 4,820,880 A | 4/1989 | Urbas |
| 4,833,230 A | 5/1989 | Kiely et al. |
| 4,843,173 A | 6/1989 | Saito et al. |
| 4,845,208 A | 7/1989 | Fuertes et al. |
| 4,900,407 A | 2/1990 | Saito et al. |
| 4,912,237 A | 3/1990 | Zeitsch |
| 4,971,657 A | 11/1990 | Avignon et al. |
| 4,977,283 A | 12/1990 | Leupold et al. |
| 5,071,754 A | 12/1991 | Walkup et al. |
| 5,132,452 A | 7/1992 | Deller et al. |
| 5,132,456 A | 7/1992 | King et al. |
| 5,149,680 A | 9/1992 | Kitson et al. |
| 5,196,617 A | 3/1993 | Kovenklioglu et al. |
| 5,247,012 A | 9/1993 | Vyvoda |
| 5,252,473 A | 10/1993 | Walkup et al. |
| 5,264,624 A | 11/1993 | Vogtel et al. |
| 5,276,240 A | 1/1994 | Timmons et al. |
| 5,281,647 A | 1/1994 | Eapen |
| 5,290,852 A | 3/1994 | Vyvoda |
| 5,359,137 A | 10/1994 | Burke |
| 5,426,219 A | 6/1995 | Lehnhardt et al. |
| 5,426,252 A | 6/1995 | Sherif |
| 5,430,214 A | 7/1995 | Smith et al. |
| 5,434,233 A | 7/1995 | Kiely et al. |
| 5,484,914 A | 1/1996 | Skibida et al. |
| 5,487,987 A | 1/1996 | Frost et al. |
| 5,516,960 A | 5/1996 | Robinson |
| 5,562,777 A | 10/1996 | Farone et al. |
| 5,599,977 A | 2/1997 | Kiely et al. |
| 5,616,496 A | 4/1997 | Frost et al. |
| 5,625,110 A | 4/1997 | Schoedel et al. |
| 5,683,952 A | 11/1997 | Onozawa et al. |
| 5,721,189 A | 2/1998 | Zhang |
| 5,726,046 A | 3/1998 | Farone et al. |
| 5,731,467 A | 3/1998 | Fleche |
| 5,766,439 A | 6/1998 | Eyal et al. |
| 5,772,013 A | 6/1998 | Kunz et al. |
| 5,773,677 A | 6/1998 | Lansink-Rotgerink et al. |
| 5,789,333 A | 8/1998 | Angelici et al. |
| 5,811,628 A | 9/1998 | Weber et al. |
| 5,820,687 A | 10/1998 | Farone et al. |
| 5,900,511 A | 5/1999 | Sengupta et al. |
| 5,919,994 A | 7/1999 | Rao |
| 5,922,635 A | 7/1999 | Olah et al. |
| 5,981,420 A | 11/1999 | Nakano et al. |
| 5,986,127 A | 11/1999 | Ionkin et al. |
| 5,998,657 A | 12/1999 | Gogate et al. |
| 6,008,418 A | 12/1999 | Baur et al. |
| 6,028,025 A | 2/2000 | Ying et al. |
| 6,049,004 A | 4/2000 | Kiely et al. |
| 6,087,296 A | 7/2000 | Harper |
| 6,127,585 A | 10/2000 | Duzick et al. |
| 6,147,208 A | 11/2000 | Achhammer et al. |
| 6,180,830 B1 | 1/2001 | Jacquot |
| 6,228,800 B1 | 5/2001 | Yamaguchi et al. |
| 6,232,264 B1 | 5/2001 | Lukehart et al. |
| 6,391,821 B1 | 5/2002 | Satoh et al. |
| 6,403,521 B1 | 6/2002 | Ishii et al. |
| 6,436,866 B1 | 8/2002 | Nishikido et al. |
| 6,441,202 B1 | 8/2002 | Lightner |
| 6,444,608 B1 | 9/2002 | Oki et al. |
| 6,462,220 B1 | 10/2002 | Luyken et al. |
| 6,476,260 B1 | 11/2002 | Herrmann et al. |
| 6,495,730 B1 | 12/2002 | Konishi et al. |
| 6,498,269 B1 | 12/2002 | Merbouh et al. |
| 6,500,649 B2 | 12/2002 | Fouache et al. |
| 6,518,440 B2 | 2/2003 | Lightner |
| 6,521,779 B1 | 2/2003 | Boschat et al. |
| 6,559,275 B2 | 5/2003 | Minami et al. |
| 6,569,670 B2 | 5/2003 | Anderson et al. |
| 6,569,802 B2 | 5/2003 | Ionkin |
| 6,692,578 B2 | 2/2004 | Schmidt et al. |
| 6,716,339 B2 | 4/2004 | Liu et al. |
| 6,743,928 B1 | 6/2004 | Zeitsch |
| 6,773,512 B2 | 8/2004 | Ennelin et al. |
| 6,894,135 B2 | 5/2005 | Kiely et al. |
| 6,894,160 B2 | 5/2005 | Capan et al. |
| 6,897,338 B2 | 5/2005 | Zhong et al. |
| 6,953,873 B2 | 10/2005 | Cortright et al. |
| 6,958,405 B2 | 10/2005 | Le-Khac et al. |
| 7,084,090 B2 | 8/2006 | Ishii et al. |
| 7,115,541 B2 | 10/2006 | Ishii et al. |
| 7,138,035 B2 | 11/2006 | Cui et al. |
| 7,161,005 B2 | 1/2007 | Schlingloff et al. |
| 7,166,743 B2 | 1/2007 | Zhong et al. |
| 7,179,366 B2 | 2/2007 | Harle et al. |
| 7,317,116 B2 | 1/2008 | Sanborn |
| 7,344,696 B2 | 3/2008 | Canos et al. |
| 7,354,743 B2 | 4/2008 | Vlasenko et al. |
| 7,364,880 B2 | 4/2008 | Ray et al. |
| 7,371,894 B2 | 5/2008 | Wonders et al. |
| 7,385,081 B1 | 6/2008 | Gong |
| 7,393,676 B2 | 7/2008 | Gokarn et al. |
| 7,399,855 B2 | 7/2008 | Frost |
| 7,411,078 B2 | 8/2008 | Miura et al. |
| 7,413,882 B2 | 8/2008 | Berka et al. |
| 7,432,382 B2 | 10/2008 | Sanborn et al. |
| 7,459,597 B2 | 12/2008 | Koivusalmi et al. |
| 7,517,675 B2 | 4/2009 | Vercauteren et al. |
| 7,572,925 B2 | 8/2009 | Dumesic et al. |
| 7,579,489 B2 | 8/2009 | Sanborn |
| 7,579,490 B2 | 8/2009 | Sanborn et al. |
| 7,582,444 B2 | 9/2009 | Hughes |
| 7,608,689 B2 | 10/2009 | Harris et al. |
| 2002/0111458 A1 | 8/2002 | Minami et al. |
| 2003/0015457 A1 | 1/2003 | Liu et al. |
| 2005/0009694 A1 | 1/2005 | Watts et al. |
| 2005/0233423 A1 | 10/2005 | Berka et al. |
| 2005/0272134 A1 | 12/2005 | Hughes |
| 2006/0084800 A1 | 4/2006 | Chenault |
| 2006/0084817 A1 | 4/2006 | Chenault |
| 2007/0027341 A1 | 2/2007 | Rossi et al. |
| 2007/0031918 A1 | 2/2007 | Dunson, Jr. et al. |
| 2007/0031919 A1 | 2/2007 | Dunson, Jr. et al. |
| 2007/0111294 A1 | 5/2007 | Burgard et al. |
| 2007/0193960 A1 | 8/2007 | Frank et al. |
| 2007/0215484 A1 | 9/2007 | Peterson et al. |
| 2007/0219397 A1 | 9/2007 | Holladay et al. |
| 2007/0287845 A1 | 12/2007 | Lilga et al. |
| 2008/0033187 A1 | 2/2008 | Zhao et al. |
| 2008/0033188 A1 | 2/2008 | Dumesic et al. |
| 2008/0033205 A1 | 2/2008 | Kiely et al. |
| 2008/0041366 A1 | 2/2008 | Wahnon |
| 2008/0096242 A1 | 4/2008 | Sanders et al. |
| 2008/0103232 A1 | 5/2008 | Lake et al. |
| 2008/0103318 A1 | 5/2008 | Lilga et al. |
| 2008/0103340 A1 | 5/2008 | Binder et al. |
| 2008/0206562 A1 | 8/2008 | Stucky et al. |
| 2008/0216391 A1 | 9/2008 | Cortright et al. |
| 2008/0293109 A1 | 11/2008 | Berka et al. |
| 2008/0300434 A1 | 12/2008 | Cortright et al. |
| 2008/0300435 A1 | 12/2008 | Cortright et al. |
| 2009/0018300 A1 | 1/2009 | Bloom et al. |
| 2009/0047719 A1 | 2/2009 | Burgard et al. |
| 2009/0131259 A1 | 5/2009 | Kiely et al. |
| 2009/0171037 A1 | 7/2009 | Aoshima et al. |
| 2009/0211942 A1 | 8/2009 | Cortright et al. |
| 2009/0215128 A1 | 8/2009 | Vlasenko et al. |
| 2009/0250653 A1 | 10/2009 | Kiely et al. |
| 2009/0255171 A1 | 10/2009 | Dumesic et al. |

(56) References Cited

U.S. PATENT DOCUMENTS

| | | |
|---|---|---|
| 2009/0270245 A1 | 10/2009 | Kumar et al. |
| 2009/0305364 A1 | 12/2009 | Burgard et al. |
| 2010/0113263 A1 | 5/2010 | Lee et al. |

FOREIGN PATENT DOCUMENTS

| | | |
|---|---|---|
| DE | 19609069 A1 | 9/1997 |
| EP | 0096913 A1 | 12/1983 |
| EP | 0151498 A2 | 8/1986 |
| EP | 1728844 A1 | 12/2006 |
| EP | 2033958 A1 | 3/2009 |
| FR | 2556344 A1 | 6/1985 |
| FR | 2663933 A1 | 1/1992 |
| FR | 2664273 A1 | 1/1992 |
| FR | 2669635 A1 | 5/1992 |
| GB | 591858 | 9/1947 |
| GB | 600871 | 4/1948 |
| GB | 876463 | 9/1961 |
| GB | 1044883 | 10/1966 |
| JP | 33-7620 | 8/1958 |
| JP | 53-144506 | 12/1978 |
| JP | 55-013243 | 1/1980 |
| JP | 59-190984 | 10/1984 |
| JP | 2-088569 A | 3/1990 |
| JP | 2001-316311 A | 11/2001 |
| JP | 2002-308819 A | 10/2002 |
| JP | 2005-060447 A | 3/2005 |
| JP | 2005-200321 A | 7/2005 |
| JP | 2005-232116 A | 9/2005 |
| JP | 2007-145736 A | 6/2007 |
| LV | 10857 | 8/1996 |
| WO | 8201701 A1 | 5/1982 |
| WO | 9421690 A2 | 9/1994 |
| WO | 9507996 A1 | 3/1995 |
| WO | 9604224 A1 | 2/1996 |
| WO | 9638402 A1 | 12/1996 |
| WO | 2005003072 A1 | 1/2005 |
| WO | 2006005070 A1 | 1/2006 |
| WO | 2006100584 A2 | 9/2006 |
| WO | 2006119357 A2 | 11/2006 |
| WO | 2007075370 A2 | 7/2007 |
| WO | 2007075476 A2 | 7/2007 |
| WO | 2007089677 A2 | 8/2007 |
| WO | 2007141293 A1 | 12/2007 |
| WO | 2008021054 A2 | 2/2008 |
| WO | 2008070762 A1 | 6/2008 |
| WO | 2008109877 A1 | 9/2008 |
| WO | 2008144514 A2 | 11/2008 |

OTHER PUBLICATIONS

Database Caplus Chemical Abstracts Service, Columbus, Ohio, US; Database Accession No. 1987:477541, Abstract of Bitsi et al., Journal of Organometallic Chemistry (1986), 310(1), 115-19.

White, J.M., et al. Opportunities for Catalysis in the 21st Century, 2002, BESAC Committee Report, 47 Pages.

Abbadi, A., et al., "Effect of pH in the Pt-Catalyzed Oxidation of D-Glucose to D-Gluconic Acid," 1995, J. Mol. Catal. A: Chem., 97:111-118.

Abbadi, A., et al., "Highly Selective Oxidation of Aldonic Acids to 2-Keto-Aldonic Acids Over Pt-Bi and Pt-Pb Catalysts," 1995, App. Catal. A: General, 124:409-417.

Blanc, B., et al., "Starch-Derived Polyols for Polymer Technologies: Preparation by Hydrogenolysis on Metal Catalysts," Apr. 2000, Green Chemistry, pp. 89-91.

Brown, J.M., Equilibration of D-Glucaric Acid in Aqueous Solution, 2007, Thesis, University of Waikato, 191 pages.

Dirkx, J., et al., "The Oxidation of Glucose with Platinum on Carbon as Catalyst," 1981, J. Catal., 67:1-13.

Dirkx, J., et al., "The Oxidation of Gluconic Acid with Platinum on Carbon as Catalyst," 1981, J. Catal., 67:14-20.

Gehret, T. et al., "Convenient Large-Scale Synthesis of D-Glucaro-1,4:6,3-dilactone," 2009, J. Org. Chem., 74 (21), pp. 8373-8376.

Koso, S., et al., "Chemoselective Hydrogenolysis of Tetrahydrofurfuryl Alcohol to 1,5-Pentanediol," 2009, Chem. Commun., 2035-2037.

Koso, S., et al., "Promoting Effect of Mo on the Hydrogenolysis of Tetrahydrofurfuryl Alcohol to 1,5-pentanediol Over Rh/SiO2," 2009, J. Catal., 267:89-92.

Abstract of BG 100407, EPISUCRES SA, 1997, 1 page.

Saha, B.C., "Hemicellulose Bioconversion," J. Ind. Microbiol. Biotechnol., 2003, 30:279-291.

Venema, F., et al., "Platinum-Catalyzed Oxidation of Aldopentoses to Aldaric Acids," 1992, J. Mol. Catal., 77:75-85.

Wang, T., et al., "Aqueous-Phase Aerobic Oxidation of Alcohols by Soluble Pt Nanoclusters in the Absence of Base," 2007, Chem. Commun., 4375-4377.

Wang T., et al., "Base-free Aqueous-Phase Oxidation of Non-Activated Alcohols with Molecular Oxygen on Soluble Pt Nanoparticles," 2009, Green Chem, 11:562-568.

Besson, M., et al., "Oxidation of Glucose and Gluconate on Pt, Pt Bi, and Pt Au Catalysts," 1996, Recueil des Travaux chimiques des pays-Bas, 115:217-221.

De La Motte, H., "Ueber die Einwirkung von Phosphorpentachlorid und Jodwasserstoffsaure auf Zuckersaure," 1879, Berichte Der Deutschen Chemischen Gesellschaft, 12/2:1571-1573.

Fischer, E., et al., "Ueber eine neue Pentonsaure und die zweite inactive Trioxyglutarsaure," 1891, Berichte Der Deutschen Chemischen Gesellschaft, 24/2:4216-4225.

Tiemann, F., et al., "Ueber Isozuckersaure," 1886, Berichte Der Deutschen Chemischen Gesellschaft, 19/1:1257-1281.

"Roadmap for Biomass Technologies in the United States," Dec. 2002, U.S. Dept. of Energy, 48 pages.

"Top Value Added for Chemicals from Biomass—Volume 1: Results of Screening for Potential Candidates from Sugars and Synthesis Gas," 2004, Produced by PNNL, NREL and EERE, T. Werpy and G. Petersen, Eds., U.S. Dept. of Energy, 76 pages.

"Acidum Tartaricum (U.S.P.)—Tartaric Acid," Feb. 4, 2010, Henriette's Herbal Homepage, www.henriettesherbal.com/eclectic/kings/acidum-tart.html, 5 pages.

International Search Report issued in PCT/US2010/038419, dated Jan. 31, 2011, 7 pages.

Written Opinion issued in PCT/US2010/038419, dated Jan. 31, 2011, 14 pages.

International Search Report issued in PCT/US2010/038422, dated Sep. 16, 2010, 6 pages.

Written Opinion issued in PCT/US2010/038422, dated Sep. 16, 2010, 11 pages.

International Search Report issued in PCT/US2010/038408, dated Feb. 2, 2011, 7 pages.

Written Opinion issued in PCT/US2010/038408, dated Feb. 2, 2011, 16 pages.

Casanova, O., et al, "Biomass into Chemicals: Aerobic Oxidation of 5-Hydroxymethyl-2-Furfural into 2,5-Furandicarboxylic Acid with Gold Nanoparticle Catalysts," 2009, ChemSusChem, 2:1138-1144.

Clarke, J.K.A., et al, "Preparation of Supported Platinum-Gold Catalysts and Alkane Reactions on Selected Platinum and Platinum-Gold Supported Clusters," 1984, App Catalysis, 9:85-108.

Dimitratos, N., et al, "Synergetic Effect of Platinum or Palladium on Gold Catalyst in the Selective Oxidation of D-Sorbitol," 2005, Catalysis Letters, 99:3-4:181-185.

Dirkx, J., et al., "The Preparation of D-Glucaric Acid by the Oxidation of D-Gluconic Acid Catalysed by Platinum on Carbon," 1977, Carbohydrate Research, 59:63-72.

Ibert, M., et al., "Determination of the Side-Products Formed During the Nitroxide-Mediated Bleach Oxidation of Glucose to Glucaric Acid," 2002, Carbohydrate Res, 337:1059-1063.

Lewkowski, J., "Synthesis, Chemistry and Applications of 5-Hydroxymethylfurfural and its Derivatives," 2001, Arkivoc (i):17-54.

Mallat, T., et al., "Oxidation of Alcohols with Molecular Oxygen on Solid Catalysts," 2004, Chem Rev, 104:3037-3058.

Mamman, A.S., et al. "Furfural: Hemicellulose/xylose-Derived Biochemical," 2008, Biofuels, Bioprod. Bioref., 2:438-454.

(56) References Cited

OTHER PUBLICATIONS

Mehltretter, C.L., et al., "Sugar Oxidation, Saccharic and Oxalic Acids by the Nitric Acid Oxidation of Dextrose," 1953, Ag and Food Chem, 1/12:779-783.

Merbouh, N., et al., "Facile Nitroxide-mediated Oxidations of D-Glucose to D-Glucaric Acid," 2001, Carbohydrate Res, 336:75-78.

Moore, J.A., et al., "An Improved Hydrogenation for the Preparation of Tetrahydrofuran cis-2,5-Dicarboxylic Acid," 1972, Organic Preparations and Procedures Int., 4/6:289-292.

Moreau, C., et al., "Recent Catalytic Advances in the Chemistry of Substituted Furans from Carbohydrates and in the Ensuing Polymers," 2004, Topics in Catalysis, 27/1-4:11-30.

Niu, W., et al., "Benzene-Free Synthesis of Adipic Acid," 2002, Biotechnol Prog, 18:201-211.

Ortiz-Soto, L.B., et al., "Structure-Sensitivity of Propylene Hydrogenation Over Cluster-Derived Bimetallic Pt-Au Catalysts," 2006, Catalysis Letters, 107/1-2:13-17.

Pamuk, V., et al., "The Preparation of D-Glucaric Acid by Oxidation of Molasses in Packed Beds," 2001, J Chem Technol Biotechnol, 76:186-190.

Prati, L., et al., "Effect of Gold Addition on Pt and Pd Catalysts in Liquid Phase Oxidations," 2007, Topics in Catalysis, 44/1-2:319-324.

Röper, H., "Selective Oxidation of D-Glucose: Chiral Intermediates for Industrial Utilization," 1991, Carbohydrates As Organic Raw Materials, F.W. Lichtenhaler (Ed), Verlag Chemie, Weinheim, Germany, pp. 267-288.

Shen, Y., et al., "Efficient Synthesis of Lactic Acid by Aerobic Oxidation of Glycerol on Au-Pt/TiO2 Catalysts," 2010, Chem Eur J, 16:7368-7371.

Smits, P.C.C., et al., "The Selective Oxidation of Aldoses and Aldonic Acids to 2-Ketoaldonic Acids with Lead-Modified Platinum-on-Carbon Catalysts," 1986, Carbohydrate Res, 153:227-235.

Smits, P.C.C., et al., "Lead Modified Platinum on Carbon Caralysts for the Selective Oxidation of (2-) Hydroxycarbonic Acids, and Especially Polyhydroxycarbonic Acids to Their 2-Keto Derivatives," 1987, App Catalysis, 33:83-96.

Thaburet, J-F., et al., "Tempo-mediated Oxidation of Maltodextrins and D-Glucose: Effect of pH on the Selectivity and Sequestering Ability of the Resulting Polycarboxylates," 2001, Carbohydrate Res, 330:21-29.

Wenkin, M., et al., "Influence of Metallic Precursors on the Properties of Carbon-Supported Bismuth-Promoted Palladium Catalysts for the Selective Oxidation of Glucose to Gluconic Acid," 1996, App Catalysis A: General, 148:181-199.

Yong, G., et al., "Efficient Catalytic System for the Selective Production of 5-Hydroxymethylfurfural from Glucose and Fructose," 2008, Angew Chem Int Ed, 47:9345-9348.

Dijkgraaf, P.J.M., "Oxidation of Glucose to Glucaric Acid by Pt/C Catalysts," 1989, 105 pages, Thesis, Technische Universiteit Eindhoven.

Lichtenthaler, F.W., et al., "Carbohydrates as Green Raw Materials for the Chemical Industry," 2004 C.R. Chimie 7:65-90.

Merbouh, N., et al., "4-AcNH-TEMPO-Catalyzed Oxidation of Aldoses to Aldaric Acids Using Chlorine or Bromine as Terminal Oxidants," 2002, J Carbohydrate Chem, 21/1&2: 65-77.

International Search Report issued in PCT/US2010/060143 dated Apr. 5, 2011, 6 pages.

Written Opinion issued in PCT/US2010/060143 dated Apr. 5, 2011, 9 pages.

Scifinder Search Results on "Xylaric Acid"—search conducted on Mar. 15, 2010, 11 Pages.

Gao, S., et al., "Low-Molecular-Weight and Oligomeric Components in Secondary Organic Aerosol from the Ozonolysis of Cycloalkenes and α-Pinene," 2004, J Phys Chem A, 108:10147-10164.

Guneral, F., et al., "Age-Related Reference Values for Urinary Organic Acids in a Healthy Turkish Pediatric Population," 1994, Clin Chem, 40(6):862-868.

Pankow, J.F., et al., "Modeling the Formation of Secondary Organic Aerosol. 1. Application of Theoretical Principles to Measurements Obtained in the α-Pinene/, β-Pinene/, Sabinene/, Δ3-Carene/, and Cyclohexene/Ozone Systems," 2001, Environ Sci Technol, 35:1164-1172.

Yang, L., et al., "Photooxidation of Dicarboxylic Acids-Part II: Kinetics, Intermediates and Field Observations," 2008, Atmospheric Environment, 42:868-880.

"Adipic Acid," compounds 24,052-4 and A2,635-7 in Aldrich Handbook of Fine Chemicals and Laboratory Equipment, Nederlands Edition, 2000, p. 40, Sigma-Aldrich, USA.

International Search Report issued in PCT/US2010/060147 dated Apr. 29, 2011, 4 pages.

Written Opinion issued in PCT/US2010/060147 dated Apr. 29, 2011, 10 pages.

Habrioux, A., et al., "Activity of Platinum-Gold Alloys for Glucose Electrooxidation in Biofuel Cells," 2007, J Phys Chem B, 111:10329-10333.

Kerzenmacher, S., et al., "Energy Harvesting by Implantable Abiotically Catalyzed Glucose Fuel Cells," 2008, J Power Sources, 182:1-17.

Second Written Opinion issued in PCT/US2010/060143 dated May 30, 2012, 6 pages.

Satoh, S., et al., "Electrochemical Reductive Cyclization of Dimethyl Dibromoalkanedioates," 1980, Hok Kaido Dai gaku Kogakubu KenKyu Hokoku, 102:33.

* cited by examiner

ADIPIC ACID COMPOSITIONS

REFERENCE TO RELATED APPLICATIONS

This application is a continuation-in-part of U.S. application Ser. No. 12/814,188, filed Jun. 11, 2010, and claims the benefit of U.S. Provisional Application Ser. No. 61/311,190, filed Mar. 5, 2010, the entire contents of which are incorporated herein by reference.

FIELD OF THE INVENTION

The present invention is directed to compositions of matter comprising an adipic acid product of formula (1)

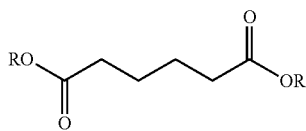

1 wherein R is independently a salt-forming ion, hydrogen, hydrocarbyl, or substituted hydrocarbyl, and at least one constituent selected from the group consisting of formula (2)

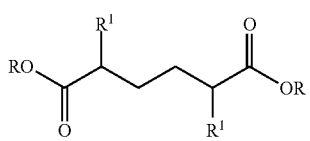

2 wherein R is as defined above, $R^1$ is H, OH, acyloxy or substituted acyloxy provided, however, at least one of $R^1$ is OH, and formula (3)

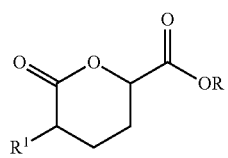

3 wherein R is as above defined and $R^1$ is H, OH, acyloxy or substituted acyloxy.

The present invention is also directed to compositions of matter comprising an adipic acid product of formula (1) and at least two different constituents selected from the group of formula (2) and formula (3), above.

The present invention includes compositions of matter comprising at least about 99 wt % adipic acid or a salt thereof and up to about 1 wt % of at least one constituent of formula (2).

The present invention further includes compositions of matter comprising at least about 99 wt % adipic acid and up to about 1 wt % of at least one constituent selected from the group consisting of formula (2) and formula (3).

The present invention further includes compositions of matter comprising at least about 99 wt % adipic acid and up to about 1 wt % of at least two constituents selected from the group consisting of formula (2) and formula (3).

The present invention also relates to industrial chemicals such as adiponitrile, hexamethylene diamine, caprolactam, caprolactone, 1,6-hexanediol, adipate esters, polyamides (e.g., nylons) and polyesters produced from such compositions of matter.

BACKGROUND OF THE INVENTION

Crude oil is currently the source of most commodity and specialty organic chemicals. Many of these chemicals are employed in the manufacture of polymers and other materials. Examples include ethylene, propylene, styrene, bisphenol A, terephthalic acid, adipic acid, caprolactam, hexamethylene diamine, adiponitrile, caprolactone, acrylic acid, acrylonitrile, 1,6-hexanediol, 1,3-propanediol, and others. Crude oil is first refined into hydrocarbon intermediates such as ethylene, propylene, benzene, and cyclohexane. These hydrocarbon intermediates are then typically selectively oxidized using various processes to produce the desired chemical. For example, crude oil is refined into cyclohexane which is then selectively oxidized to "KA oil" which is then further oxidized for the production of adipic acid, an important industrial monomer used for the production of nylon 6,6. Many known processes are employed industrially to produce these petrochemicals from precursors found in crude oil. For example, see *Ullmann's Encyclopedia of Industrial Chemistry*, Wiley 2009 (7th edition), which is incorporated herein by reference. Chemicals produced from crude oil, and the downstream products thereof, exhibit no C-14 constituents.

For many years there has been an interest in using biorenewable materials as a feedstock to replace or supplement crude oil. See, for example, Klass, Biomass for Renewable Energy, Fuels, and Chemicals, Academic Press, 1998, which is incorporated herein by reference. Moreover, there have been efforts to produce adipic acid from renewable resources using processes involving a combination of biocatalytic and chemocatalytic processes. See, for example, "Benzene-Free Synthesis of Adipic Acid", Frost et al. Biotechnol. Prog. 2002, Vol. 18, pp. 201-211, and U.S. Pat. Nos. 4,400,468, and 5,487,987. Unlike products produced from crude oil, products produced from biorenewable materials, more particularly from carbohydrates derived therefrom, exhibit distinctly different characteristics, among which is the presence of C-14 constituents.

Until the discovery of the processes disclosed in co-pending U.S. application Ser. No. 12/814,188, filed Jun. 11, 2010, by Boussie et al., one of the major challenges for converting biorenewable resources such as carbohydrates (e.g. glucose derived from starch, cellulose or sucrose) to current commodity and specialty chemicals was the selective removal of oxygen atoms from the carbohydrate.

SUMMARY OF THE INVENTION

Briefly, the present invention is directed to compositions of matter comprising an adipic acid product of formula (1)

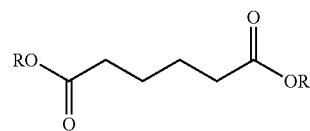

1 wherein R is independently a salt-forming ion, hydrogen, hydrocarbyl, or substituted hydrocarbyl, and at least one constituent selected from the group consisting of formula (2)

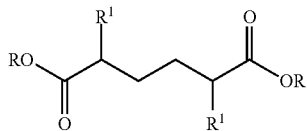

wherein R is as defined above and each of $R^1$ is H, OH, acyloxy or substituted acyloxy provided, however, that at least one of $R^1$ is OH, and formula (3)

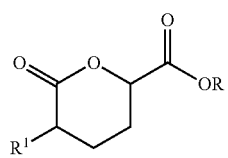

wherein R is as defined above and $R^1$ is H, OH, acyloxy or substituted acyloxy.

The present invention is also directed to compositions of matter comprising an adipic acid product of formula (1) and at least two different constituents selected from the group of formula (2) and formula (3), above.

The present invention includes compositions of matter comprising at least about 99 wt % adipic acid or a salt thereof and up to about 1 wt % of at least one constituent of formula (2).

The present invention further includes compositions of matter comprising at least about 99 wt % adipic acid and up to about 1 wt % of at least one constituent selected from the group consisting of formula (2) and formula (3).

The present invention further includes compositions of matter comprising at least about 99 wt % adipic acid and up to about 1 wt % of at least two constituents selected from the group consisting of formula (2) and formula (3).

The present invention also relates to industrial chemicals such as adiponitrile, hexamethylene diamine, caprolactam, caprolactone, 1,6-hexanediol, adipate esters, polyamides (e.g., nylons) and polyesters produced from such compositions of matter.

Other objects and features will become apparent and/or will be pointed out hereinafter.

DESCRIPTION OF THE PREFERRED EMBODIMENTS

In accordance with the present invention, applicants disclose compositions of matter heretofore not produced, such compositions comprising an adipic acid product of formula (1), above, and at least one constituent selected from the group consisting of formulae (2) and (3), above, and methods of producing the same. The compositions of matter of the present invention may be converted, according to processes known in the art, to various other industrially significant chemicals including, for example, adiponitrile, caprolactam, caprolactone, hexamethylene diamine, 1,6-hexanediol, adipate esters, polyamides (e.g., nylon) or polyesters.

Glucose, a preferred feedstock for producing the products of the present invention, can be obtained from various carbohydrate-containing sources including conventional biorenewable sources such as corn grain (maize), wheat, potato, cassava and rice as well as alternative sources such as energy crops, plant biomass, agricultural wastes, forestry residues, sugar processing residues and plant-derived household wastes. Glucose may be isolated from biorenewable sources using methods that are known in the art. See, for example, Centi and van Santen, *Catalysis for Renewables*, Wiley-VCH, Weinheim 2007; Kamm, Gruber and Kamm, *Biorefineries-Industrial Processes and Products*, Wiley-VCH, Weinheim 2006; Shang-Tian Yang, *Bioprocessing for Value-Added Products from Renewable Resources New Technologies and Applications*, Elsevier B. V. 2007; Furia, *Starch in the Food Industry*, Chapter 8, *CRC Handbook of Food Additives* $2^{nd}$ *Edition* CRC Press, 1973. See also chapters devoted to Starch, Sugar and Syrups within *Kirk-Othmer Encyclopedia of Chemical Technology* $5^{th}$ *Edition*, John Wiley and Sons 2001. Also, processes to convert starch to glucose are known in the art; see, for example, Schenck, "Glucose and Glucose containing Syrups" in *Ullmann's Encyclopedia of Industrial Chemistry*, Wiley-VCH 2009. Furthermore, methods to convert cellulose to glucose are known in the art, see, for example, Centi and van Santen, *Catalysis for Renewables*, Wiley-VCH, Weinheim 2007; Kamm, Gruber and Kamm, *Biorefineries-Industrial Processes and Products*, Wiley-VCH, Weinheim 2006; Shang-Tian Yang, *Bioprocessing for Value-Added Products from Renewable Resources New Technologies and Applications*, Elsevier B. V. 2007.

In accordance with the present invention, the compositions of matter of the present invention are prepared by chemocatalytic conversion of a glucose source to a hydrodeoxygenation substrate comprising at least glucaric acid and/or derivatives thereof, which substrate is subsequently converted by chemocatalytic means employing a heterogeneous catalyst comprising platinum or platinum and rhodium, in the presence of a source of bromine and in the presence of an acetic acid solvent, wherein the reaction product of the hydrodeoxygenation step is subjected to techniques commonly employed in the purification of adipic acid produced by conventional processes, such techniques including, for example, washing, crystallization and recrystallization to produce the compositions of matter of the present invention.

The hydrodeoxygenation substrate comprises a compound of the following formula (A):

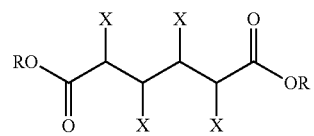

wherein X is independently hydroxyl, oxo, halo, acyloxy or hydrogen provided that at least one X is not hydrogen; R is independently a salt-forming ion, hydrogen, hydrocarbyl, or substituted hydrocarbyl; or a mono- or di-lactone thereof.

As used herein, the term "hydrocarbyl" refers to hydrocarbyl moieties, preferably containing 1 to about 50 carbon atoms, preferably 1 to about 30 carbon atoms, and even more preferably 1 to about 18 carbon atoms, including branched or unbranched, and saturated or unsaturated species. Preferred hydrocarbyl can be selected from the group consisting of alkyl, alkylene, alkoxy, alkylamino, thioalkyl, haloalkyl, cycloalkyl, cycloalkylalkyl, heterocyclyl, N-heterocyclyl, heterocyclylalkyl, aryl, aralkyl heteroaryl, N-heteroaryl, heteroarylalkyl, and the like. A hydrocarbyl may be optionally substituted hydrocarbyl. Hence, various hydrocarbyls can be further selected from substituted alkyl, substituted cycloalkyl and the like.

Salt forming ions include, without limitation, for example ammonium ions and metal ions (e.g., alkali and alkaline earth metals). When R is a salt forming ion (i.e., a cation), the carboxyl group may be considered to be anion (i.e., carboxylate anion).

In various embodiments, the hydrodeoxygenation substrate comprises a compound of formula (A), wherein X is hydroxyl and R is independently a salt-forming ion, hydrogen, hydrocarbyl, or substituted hydrocarbyl.

As shown in formula (A), the hydrodeoxygenation substrate contains a six carbon chain comprising four chiral centers. As a result several stereoisomers are possible. However, the preferred hydrodeoxygenation substrate comprises glucaric acid.

The hydrodeoxygenation substrate may also contain various ketones. For example, not wishing to be bound by theory, when glucaric acid is further oxidized, ketones such as 2-keto-glucaric acid (2,3,4-trihydroxy-5-oxohexanedioic acid) and 3-keto-glucaric acid (2,3,5-trihydroxy-4-oxohexanedioic acid) may be formed.

The hydrodeoxygenation substrate may comprise various lactones derived from glucaric acid. For example, not wishing to be bound by theory, it is believed that various mono- and di-lactones are present in equilibrium with glucaric acid in aqueous solution, including for example, D-glucaro-1,4-lactone, D-glucaro-6,3-lactone, and D-glucaro-1,4:6,3-dilactone. Moreover, processes have been developed to quantitatively convert glucaric acid or a salt thereof in solution to one or more lactones and recover a substantially pure lactone stream. For example see "Convenient Large-Scale Synthesis of D-Glucaro-1,4:6,3-dilactone" Gehret et al., J. Org. Chem., 74 (21), pp. 8373-8376 (2009). Also, lactones such as L-threo-4-deoxy-hex-4-enaro-6,3-lactone and L-erythro-4-deoxy-hex-4-enaro-6,3-lactone may form from the thermal decomposition of D-Glucaro-1,4:6,3-dilactone.

Therefore, in various embodiments, the hydrodeoxygenation substrate comprises D-glucaro-1,4-lactone. In these and other embodiments, the hydrodeoxygenation substrate comprises D-glucaro-6,3-lactone. Still further, in these and other embodiments, the hydrodeoxygenation substrate comprises D-glucaro-1,4:6,3-dilactone. In these and other embodiments, the hydrodeoxygenation substrate comprises L-threo-4-deoxy-hex-4-enaro-6,3-lactone. Still even further, in these and other embodiments, the hydrodeoxygenation substrate comprises L-erythro-4-deoxy-hex-4-enaro-6,3-lactone.

In accordance with the present invention, the compositions of matter comprise an adipic acid product (formula 1) prepared by reacting, in the presence of a source of bromine, preferably HBr, a hydrodeoxygenation catalyst comprising platinum or platinum and rhodium and a solvent, preferably acetic acid, a hydrodeoxygenation substrate (formula A) and hydrogen, according to the following reaction:

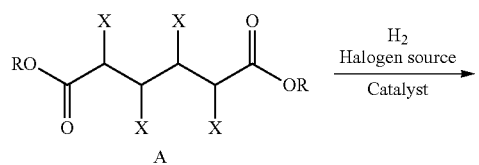

-continued

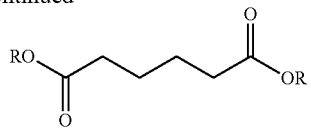

wherein X and R are defined as described above, and at least one constituent selected from the group consisting of formula (2)

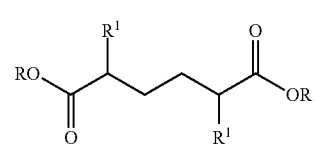

wherein R is as defined above and each of $R^1$ is, independently, H, OH, acyloxy or substituted acyloxy provided, however, that at least one of $R^1$ is OH, and formula (3)

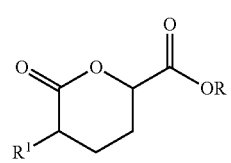

wherein R is as defined above and R1 is H, OH, acyloxy or substituted acyloxy.

In preferred embodiments, the compositions of matter comprise adipic acid and/or salt thereof and at least two other constituents selected from formulae (2) and (3), above.

In certain preferred embodiments, the compositions of matter comprises at least about 99% adipic acid or salt thereof and up to 1% of at least one constituent selected from formula (2) and formula (3), above.

In certain preferred embodiments, the compositions of matter comprises at least about 99% adipic acid or salt thereof and up to 1% of at least one constituent of formula (2), above.

In certain preferred embodiments, the compositions of matter comprises at least about 99% adipic acid or salt thereof and up to 1% of at least two constituents selected from formula (2) and formula (3), above.

It should be recognized that the hydrodeoxygenation reaction can be conducted by first forming and optionally purifying or isolating various intermediates formed by combining a hydrodeoxygenation substrate and the source of bromine and subsequently reacting the intermediate with hydrogen in the presence of the hydrodeoxygenation catalyst and, optionally, in the absence of any additional halogen source. In various embodiments, the hydrodeoxygenation substrate is halogenated with hydrobromic acid to form a brominated intermediate (e.g., an alkyl bromide). In other embodiments, the hydrodeoxygenation substrate is halogenated with a molecular bromine to form the brominated intermediate (e.g., an alkyl bromide).

The bromine source may be in a form selected from the group consisting of atomic, ionic, molecular, and mixtures thereof. The bromine source is most preferably hydrogen bromide.

The molar ratio of bromine to the hydrodeoxygenation substrate is less than 1. In various embodiments, the mole ratio of halogen to the hydrodeoxygenation substrate is typically less than about 0.5.

Generally, the reaction allows for recovery of the bromine, and catalytic quantities of bromine can be used, recovered and recycled for continued use.

The temperature of the hydrodeoxygenation reaction mixture is preferably between about 100° C. and 180° C.

Typically, the partial pressure of hydrogen is in the range of about 800 psia (5516 kPa) to about 1300 psia (8964 kPa).

The hydrodeoxygenation reaction is conducted in the presence of solvents. Mixtures of water and weak carboxylic acid, or weak carboxylic acid are suitable solvents. Preferably, the weak carboxylic acid is acetic acid.

In general, the reaction can be conducted in a batch, semi-batch, or continuous reactor design using fixed bed reactors, trickle bed reactors, slurry phase reactors, moving bed reactors, or any other design that allows for heterogeneous catalytic reactions. Examples of reactors can be seen in *Chemical Process Equipment—Selection and Design*, Couper et al., Elsevier 1990, which is incorporated herein by reference. It should be understood that the hydrodeoxygenation substrate, halogen source, hydrogen, any solvent, and the hydrodeoxygenation catalyst may be introduced into a suitable reactor separately or in various combinations.

The hydrodeoxygenation catalyst is a solid-phase heterogeneous catalyst comprising platinum, or platinum and rhodium, present on a support (preferably, at one or more surfaces, external or internal). Typically, the metals constitute not more than about 8%, preferably less than or equal to about 4%.

The Pt:Rh molar ratio may vary, for example, from about 20:1 to about 0.1:1, from about 10:1 to about 0.5:1, and, more preferably, from about 5:1 to about 1:1.

Preferred catalyst supports include carbon, silica, titania, zirconia, zeolite, clays, silicon carbide, and modifications, mixtures or combinations thereof. The preferred supports may be modified through methods known in the art such as, for example, heat treatment, acid treatment or the introduction of a dopant. In various preferred embodiments, the hydrodeoxygenation catalyst support is selected from the group consisting of silica, zirconia and titania. More preferred catalysts comprise platinum and rhodium on a support comprising silica.

The metals may be deposited on the support using procedures known in the art including, but not limited to incipient wetness, ion-exchange, deposition-precipitation and vacuum impregnation. The metals may be deposited sequentially or simultaneously. In various embodiments, following metal deposition, the catalyst is dried at a temperature of at least about 50° C., more typically at least about 120° C. or more for a period of time of at least about 1 hour, more typically at least about 3 hours or more. In these and other embodiments, the catalyst is dried under sub-atmospheric conditions. In various embodiments, the catalyst is reduced after drying (e.g., by flowing 5% $H_2$ in $N_2$ at 350° C. for 3 hours). Still further, in these and other embodiments, the catalyst is calcined, for example, at a temperature of at least about 500° C. for a period of time (e.g., at least about 3 hours).

The compositions of matter of the present invention may be recovered from the hydrodeoxygenation reaction mixture by one or more conventional methods known in the art including, for example, solvent extraction, crystallization or evaporative processes. The reaction product recovered from the hydrodeoxygenation reaction comprises adipic acid product and, typically, several of the additional constituents of formulae (2) and/or (3), above, in liquid form. The recovered reaction product is dried. Drying can be conducted in any suitable inert atmosphere, in air or under a vacuum. The temperature at which drying should be sufficient such that the compositions of matter will precipitate out of solution. Typically, the temperature will be in the range of about 25° C. to about 120° C. The precipitate may then be subjected to conventional treatments employed for the recovery of adipic acid produced by conventional processes, such treatments including, for example, washing, for example, with water followed by, for example, redissolution and recrystallization (one or more additional times), followed by a decolorization treatment and, for example, a final recrystallization and wash.

Downstream Chemical Products

Various methods are known in the art for conversion of adipic acid to downstream chemical products or intermediates including adipate esters, polyesters, adiponitrile, hexamethylene diamine (HMDA), caprolactam, caprolactone, 1,6-hexanediol, aminocaproic acid, and polyamide such as nylons. For conversions from adipic acid, see for example, without limitation, U.S. Pat. Nos. 3,671,566, 3,917,707, 4,767,856, 5,900,511, 5,986,127, 6,008,418, 6,087,296, 6,147,208, 6,462,220, 6,521,779, 6,569,802, and Musser, "Adipic Acid" in *Ullmann's Encyclopedia of Industrial Chemistry*, Wiley-VCH, Weinheim, 2005.

In various embodiments, the compositions of matter of the present invention comprising at least about 99 wt % adipic acid can be converted to adiponitrile. Adiponitrile can be used industrially for the manufacture of hexamethylene diamine, see Smiley, "Hexamethylenediamine" in *Ullmann's Encyclopedia of Industrial Chemistry*, Wiley-VCH 2009. Therefore, the compositions of matter of the present invention can be converted to hexamethylene diamine.

Adipic acid is useful in the production of polyamides, such as nylon 6,6 and nylon 4,6. See, for example, U.S. Pat. No. 4,722,997, and Musser, "Adipic Acid" in *Ullmann's Encyclopedia of Industrial Chemistry*, Wiley-VCH, Weinheim, 2005. The hexamethylene diamine formed from the compositions of matter of the present invention comprising at least about 99 wt % adipic acid can likewise be further used for the preparation of polyamides such as nylon 6,6 and nylon 6,12. See, for example Kohan, Mestemacher, Pagilagan, Redmond, "Polyamides" in *Ullmann's Encyclopedia of Industrial Chemistry*, Wiley-VCH, Weinheim, 2005.

Accordingly, the compositions of matter of the present invention comprising at least about 99 wt % adipic acid and a polymer precursor derived from such compositions may be reacted to produce a polyamide. Polymer precursor, as used herein, refers to a monomer which can be converted to a polymer (or copolymer) under appropriate polymerization conditions. In various embodiments, the polyamide comprises nylon 6,6. In these embodiments, the polymer precursor comprises hexamethylene diamine which may be derived from the compositions of the present invention.

In other embodiments, the compositions of matter of the present invention comprising at least about 99 wt % adipic acid may be converted to caprolactam. The caprolactam formed can be further used for the preparation of polyamides by means generally known in the art. Specifically, caprolactam can be further used for the preparation of nylon 6. See, for example Kohan, Mestemacher, Pagilagan, Redmond, "Polyamides" in *Ullmann's Encyclopedia of Industrial Chemistry*, Wiley-VCH, Weinheim, 2005.

In other embodiments, adipic acid and a polymer precursor may be reacted to produce a polyester, wherein the adipic acid product is prepared in accordance with the present invention.

In other embodiments, the compositions of matter of the present invention comprising at least about 99 wt % adipic acid may be converted to 1,6-hexanediol. 1,6-hexanediol is a valuable chemical intermediate used in the production of polyesters and polyurethanes. Accordingly, in various embodiments, polyester may be prepared by reacting the compositions of matter of the present invention comprising at least about 99 wt % adipic acid and 1,6-hexanediol derived from such compositions of the present invention.

In various embodiments a salt of adipic acid may be produce wherein the process comprises reacting the compositions of matter of the present invention comprising at least about 99 wt % adipic acid with hexamethylene diamine, thereby forming the salt.

When introducing elements of the present invention or the preferred embodiments(s) thereof, the articles "a", "an", "the" and "said" are intended to mean that there are one or more of the elements. The terms "comprising", "including" and "having" are intended to be inclusive and mean that there may be additional elements other than the listed elements.

In view of the above, it will be seen that the several objects of the invention are achieved and other advantageous results attained.

As various changes could be made in the above compositions and processes without departing from the scope of the invention, it is intended that all matter contained in the above description shall be interpreted as illustrative and not in a limiting sense.

Having described the invention in detail, it will be apparent that modifications and variations are possible without departing from the scope of the invention defined in the appended claims.

EXAMPLES

The following non-limiting examples are provided to further illustrate the present invention.

Reactions were conducted in 1 mL glass vials housed in a pressurized vessel in accordance with the procedures described in the examples below. Product yields were determined using a Dionex ICS-3000 Chromatography system. For Example 1, the products were first separated on an Ionpac® AS11-HC column and then quantified by conductivity detection through comparison with calibration standards. For Example 2, the products were first separated on an Acclaim Organic Acid column and then quantified by a UV detector through comparison with calibration standards.

Example 1

Glucose to Glucaric Acid

Several catalysts were obtained from commercial vendors: Johnson Matthey 5% Pt/C (three examples; JM-23 [B103032-5, Lot #C-9090]; JM-25 [B103014-5, Lot #C9230]; and JM-27 [B-501032-5, Lot #C-9188]), Johnson Matthey 5% Pt/Al$_2$O$_3$ (two examples; JM-32 [B301013-5, Lot #C8959] and JM-33 [B301099-5, Lot #C9218]), and BASF Escat 2351 5% Pt/SiO$_2$ [Lot #A4048107]; and 1.5% Au/TiO$_2$ [Süd Chemie 02-10]. Other catalysts were prepared in accordance with the procedure described herein.

Preparation of Supported Platinum Catalysts

Multiple portions of suitably concentrated aqueous Pt(NO$_3$)$_2$ solutions (Heraeus) were added to the appropriate support (wherein the total combined volume of the Pt(NO$_3$)$_2$ solutions was matched to equal to the pore volume of the chosen support) with agitation between additions. Post impregnation, the product was dried in a furnace at 120° C. for 12 hours, Material for catalyst testing was prepared by reduction under flowing 5 vol. % H$_2$ in N$_2$ for 3 hours at either 200° C. or 350° C. Note that this procedure was used for all supports except carbon. See the later description for the preparation of a Pt/Carbon catalyst.

Preparation of Pt/M2/Support Catalysts (M2=Mn, Co, Fe, Re, Cu)

Approximately 7-8 mg of dried supported platinum catalyst (taken post drying but prior to reduction) was dispensed into an 8×12 array containing 1 mL glass vials. To select vials within the array, 6-7 µl (where the total addition volume was matched to equal to the pore volume of the support weighed into the vial) of suitably concentrated M2 stock solutions were added (M2=Mn, Fe, Co, Re, Cu obtained from Strem or Sigma-Aldrich, see Table 1). Post M2 addition, the mixtures were agitated via a multi-tube vortexer to impregnate the supports. Post impregnation, the glass vial arrays of Pt/M2/Support catalysts were dried in a furnace at 120° C. for 1 hour, followed by calcination at 500° C. for 3 hours followed by reduction under flowing 5 vol. % H$_2$ in N$_2$ at either 200° C. or 350° C. for 3 hours. Note that this procedure was used to prepare all Pt/M2/Support catalysts with the exception of the 1.5% Pt/1.5% Au/Titania catalyst. In this case Pt(NO$_3$)$_2$ solution was added to a dried sample of the commercial 1.5% Au/Titania catalyst [Slid Chemie 02-10] (wherein the total volume of the Pt(NO$_3$)$_2$ volume was matched to equal to the pore volume of the catalyst) with agitation, whereupon the material was dried in a furnace at 120° C. for 1 hour, followed by reduction under flowing 5 vol. % H$_2$ in N$_2$ at 350° C. for 3 hours.

Preparation of 4 Wt. % Pt/Carbon Catalyst

Multiple portions of suitably concentrated aqueous Pt(NO$_3$)$_2$ solution (Heraeus) were added to 2 g of dried Degussa HP-160 furnace black carbon (3.94 mL total addition volume) with agitation between additions. Post impregnation, the 4 wt. % Pt/Carbon was dried under vacuum for one hour at 50° C., followed by reduction under flowing 5 vol. % H$_2$ in N$_2$ for three hours at 350° C.

Glucose to Glucaric Acid Reactions

Catalysts were dispensed into 1 mL vials within a 96-well reactor insert (Symyx Solutions). The reaction substrate was D-glucose (Sigma-Aldrich, 0.552M in water). To each vial was added 250 µL of glucose solution. The vials were each covered with a Teflon pin-hole sheet, a silicone pin-hole mat and steel gas diffusion plate (Symyx Solutions). The reactor insert was placed in a pressure vessel and charged three times with oxygen to 100 psig with venting after each pressurization step. The reactor was then charged to 75 psig with oxygen, or to 500 psig with air, closed and placed on a shaker, heated at the designated temperature for the specified reaction time. After the reaction time had elapsed shaking was stopped and the reactor cooled to room temperature whereupon the reactors were vented. Samples for ion-chromatography (IC) analysis were prepared by adding to each reaction vial 750 µL of a 1.067 wt. % citric acid solution (as internal standard) then the plate was covered and mixed followed by centrifugation to separate catalyst particles. Each reaction sample was further diluted by performing two 20-fold dilutions then analyzed by Ion Chromatography. In some instances, HCl was used as alternative internal standard through the addition of 100 µL of 50 ppm solution during the second 20-fold dilution. The results are presented in Table 1.

TABLE 1

| | Catalyst (wt. % M2 wt. % Pt/Support) | M1 Precursor | M2 Precursor | Temp. (° C.) | Time (Hours) | Catalyst Amount (mg) | Glucaric Acid Yield (%) |
|---|---|---|---|---|---|---|---|
| 1 | 0.06% Mn 4% Pt/Silica Davisil 635 | $Pt(NO_3)_2$ | $Mn(NO_3)_2$ | 80 | 5 | 7 | 38 |
| 2 | 0.06% Fe 4% Pt/Silica Davisil 635 | $Pt(NO_3)_2$ | $Fe(NO_3)_3$ | 80 | 5 | 8 | 28 |
| 3 | 0.06% Co 4% Pt/Silica Davisil 635 | $Pt(NO_3)_2$ | $Co(NO_3)_2$ | 80 | 5 | 8 | 34 |
| 4 | 4% Pt/Silica Davisil 635 | $Pt(NO_3)_2$ | None | 80 | 5 | 8 | 34 |
| 5 | 4% Pt/Silica 5 μm Cariact | $Pt(NO_3)_2$ | None | 90 | 5 | 8 | 50 |
| 6 | 4% Pt/Silica 5 μm Cariact | $Pt(NO_3)_2$ | None | 90 | 8 | 8 | 66 |
| 7 | 4% Pt/Silica Merck 10180 | $Pt(NO_3)_2$ | None | 90 | 5 | 8 | 40 |
| 8 | 1.91% Re 4% Pt/Silica Merck 10180 | $Pt(NO_3)_2$ | $HReO_4$ | 90 | 5 | 8 | 39 |
| 9 | 0.65% Cu 4% Pt/Silica Merck 10180 | $Pt(NO_3)_2$ | $Cu(NO_3)_2$ | 90 | 5 | 8 | 39 |
| 10 | 0.10% Mo 4% Pt/Silica Merck 10180 | $Pt(NO_3)_2$ | $(NH_4)_6Mo_7O_{24}$ | 90 | 5 | 8 | 38 |
| 11 | 4% Pt/Carbon Degussa HP-160 | $Pt(NO_3)_2$ | None | 80 | 5 | 8 | 53 |
| 12 | 4% Pt/Carbon Degussa HP-160 | $Pt(NO_3)_2$ | None | 90 | 8 | 8 | 60 |
| 13 | 5% Pt/C [JM-23] | | None | 80 | 5 | 10 | 52 |
| 14 | 5% Pt/C [JM-25] | | None | 80 | 5 | 10 | 57 |
| 15 | 5% Pt/C [JM-27] | | None | 80 | 5 | 10 | 57 |
| 16 | 5% Pt/$Al_2O_3$ [JM-32] | | None | 80 | 5 | 10 | 23 |
| 17 | 5% Pt/$Al_2O_3$ [JM-33] | | None | 80 | 5 | 10 | 31 |
| 18 | 5% Pt/$SiO_2$ [BASF Escat 2351] | $Pt(NO_3)_2$ | None | 80 | 5 | 10 | 15 |
| 19 | 8% Pt/Zirconia Daiichi Kigenso Z-1044 | $Pt(NO_3)_2$ | None | 90 | 5 | 8 | 52 |
| 20 | 8% Pt/Zirconia Daiichi Kigenso Z-1628 | $Pt(NO_3)_2$ | None | 90 | 5 | 8 | 59 |
| 21 | 8% Pt/Zirconia Ceria Daiichi Kigenso Z-1006 | $Pt(NO_3)_2$ | None | 90 | 5 | 8 | 54 |
| 22 | 8% Pt/Ceria Daiichi Kigenso Z-1627 | $Pt(NO_3)_2$ | None | 90 | 5 | 8 | 17 |
| [b]23 | [a]4% Pt/Zeolite Zeolyst CP 811C-300 | $Pt(NO_3)_2$ | None | 100 | 5 | 8 | 39 |
| [b]24 | [a]4% Pt/Titania NorPro ST 61120 | $Pt(NO_3)_2$ | None | 100 | 5 | 8 | 30 |
| [b]24 | 1.5% Pt 1.5% Au/Titania [Süd Chemie 02-10] | | $Pt(NO_3)_2$ | 100 | 5 | 8 | 55 |
| [b]25 | 4% Pt 4% Au/Titania NorPro ST 61120 | $AuCl_3$ | $Pt(NO_3)_2$ | 100 | 5 | 8 | 32 |

[a]These catalysts were calcined at 500 C. for 3 hours prior to reduction.
[b]These reactions were run under 500 psig of air, all other reactions in Table 1 were run under 75 psig of $O_2$.
Catalysts in examples 4-7, 11-12 were reduced at 200° C. under flowing 5 vol. % $H_2$ in $N_2$ for 3 hours.
Catalysts in examples 1-3, 8-10, 19-25 were reduced at 350° C. under flowing 5 vol. % $H_2$ in $N_2$ for 3 hours.
Commercial catalysts in examples 13-18 were screened directly.

Example 2

Glucaric Acid to Adipic Acid

Preparation of Pt/Rh Supported Catalyst by Co-Impregnation
8 mg of silica support (Davisil 635 W.R. Grace & Co.) was dispensed into a 1 mL glass vial. The support was dried at 120° C. for 12 hours prior to use. To the vial (where the total addition volume was matched to equal to the pore volume of the support weighed into the vial) suitably concentrated pre-mixed stock solutions were added (obtained from Heraeus). Post metal addition, the mixture was agitated via a multi-tube vortexer to impregnate the support. Post impregnation, the glass vial array of catalyst was dried in a furnace at 120° C. for 1 hour, followed by calcination at 500° C. for 3 hours. Upon cooling, the catalyst was stored in a dessicator until used.

Glucaric Acid to Adipic Acid Reaction

The catalyst was transferred to a 1 mL glass vial within a 96-well reactor insert (Symyx Solutions). The vial received a glass bead, 250 μL of 0.2 M Glucaric Acid (prepared from calcium glucarate) (Sigma-Aldrich), and 0.2 M HBr (Sigma-Aldrich) in Acetic Acid (Sigma-Aldrich). Upon solution addition, the vial was covered with a Teflon pin-hole sheet, a silicone pin-hole mat and steel gas diffusion plate (Symyx Solutions). The reactor insert was placed in a pressure vessel pressurized and vented 3 times with nitrogen and 3 times with hydrogen before being pressurized with hydrogen to 710 psig, heated to 160° C. and shaken for 3 hours. After 3 hours the reactor was cooled, vented and purged with nitrogen. 750 μl of water was then added to the vial. Following the water addition, the vial was covered and shaken to ensure adequate mixing. Subsequently, the covered vial was placed in a centrifuge to separate the catalyst particles. The reaction sample was then diluted 2-fold with water to generate a sample for analysis by HPLC. The results are presented in Table 2.

TABLE 2

| | Catalyst (wt. % M2 wt. % M1/Support) | M1 Precursor | M2 Precursor | Catalyst Amount (mg) | Adipic Acid Yield (%) |
|---|---|---|---|---|---|
| 38 | 1.65% Rh 4.7% Pt/Silica Davisil 635 | $Pt(NO_3)_2$ | $Rh(NO_3)_3$ | 8 | 89 |

Recovery of Composition of Matter of the Present Invention

Solution is collected from the outlet of a reactor. The solution is evaporated to dryness. Acetic acid is added in sufficient quantity to dissolve the material at 90° C. The dissolved material is allowed to crystallize at room temperature. Crystals are recovered by filtration and further recrystallized an additional 3 times from water using a concentration of 1 g of crystals in 5 mL of water. During a second recrystallization, the hot solution is filtered through decolorizing carbon. Finally, the crystals a dried under vacuum at 60° C. The composition is determined to be >99+ wt % purity adipic acid by $^1$H NMR. Mass spectrometry reveals peaks consistent with the presence the molecules represented by formula (2) and formula (3), above, depicted below, in cumulative amount <1.0 wt %.

Example 3

The Preparation of Adipic Acid from Glucose Using Continuous Fixed Bed Reactors

Preparation of 4 Wt. % Pt-4 Wt. % Au/Titania Catalyst
625 μl of an aqueous solution of $HAuCl_4$ (containing 22.54 wt. % Au) was added to a suspension of 5.0 g Titania ST 31119 (Saint-Gobain Norpro) in deionized water (500 ml) while stirring. The suspension was stirred at room temperature for 30 minutes. 30 ml of an aqueous solution of urea (20 wt. %) was added to above suspension and the resulting suspension was heated at 80° C. overnight with stirring. The suspension was then cooled to room temperature, centrifuged and supernatant was decanted. The light yellow solid was washed with deionized water (3×400 ml) at 50° C. before it was dried in a 60° C. oven overnight under a dry air purge. The sample was then reduced at 200° C. under a forming gas (5% $H_2$ and 95% $N_2$) atmosphere for 3 hours with 2° C./min temperature ramp rate to give 4.90 g purple solid.

1.225 ml of an aqueous solution of $Pt(NO_3)_2$ (containing 11.4 wt % Pt) was added to the purple solid in 4 portions. After each addition, the mixture was agitated to impregnate the Au-containing support. The sample was dried in a 60° C. oven overnight under a dry air purge. The sample was then reduced at 350° C. under a forming gas (5% $H_2$ and 95% $N_2$) atmosphere for 3 hours with 2° C./min temperature ramp rate. The final catalyst was composed of ca. 4.0 wt % Au and 4.0 wt % Pt.

Preparation of 2.3 Wt. % Pt-0.8 Wt. % Rh/Silica Catalyst 2 g of dried Silica Davisil 635, pore size 60 Å, 60-100 mesh (Aldrich) was weighed into a vial. A suitably concentrated Pt—Rh stock solution was prepared from concentrated acidic stock solutions purchased from Heraeus. Multiple additions of the Pt—Rh stock solution were added to the silica (silica pore volume=0.88 mL/g) until a total volume of 1.76 ml was reached. After each addition, the mixture was agitated to impregnate the silica. Post impregnation, the Pt—Rh/Silica mixtures were dried in a furnace at 120° C. for 12 hours, followed by calcination at 500° C. for 3 hours. Upon cooling the catalysts were stored in a dessicator until used.

Conversion of Glucose to Glucaric Acid

The reaction was performed in a ¼-inch OD by 401 mm long 321 stainless steel tube with 2 μm 316 stainless steel frits at both ends of the catalyst bed. Catalyst beds were vibration packed with silicon carbide (180-300 μm) at the bottom to approximately 40 mm depth followed by catalyst (1.757 g) then silicon carbide (180-300 μm) to the top. The packed reactor tube was clamped in an aluminum block heater equipped with PID controller. All reactions were performed with gas and liquid entering at the top of the reactor with the conditions described in Table 3. Gas and liquid flows were regulated by mass flow controller and HPLC pump, respectively. Glucose solutions were prepared by dissolving D-(+)-Glucose (Sigma-Aldrich, ≥99.5%) in water. A back pressure regulator controlled reactor pressure as indicated in Table 3. All reactions were performed with zero grade air (Matheson Tri-Gas, Santa Clara, Calif.). Reactor product was collected over 122 hours and concentrated under reduced pressure without further purification.

TABLE 3

| Example | Reactor temperature/ ° C. | Glucose concentration/ wt % | Reactor pressure/ psi | Liquid flowrate/μL min$^{-1}$ | Gas flowrate/ mL min$^{-1}$ (STP) | Glucose conversion/ % | Glucaric acid yield/ % |
|---|---|---|---|---|---|---|---|
| 1 | 105 | 20 | 350 | 100 | 114 | 100.0 | 59.4 |

Conversion to Adipic Acid

Product from the oxidation fixed bed reactor was concentrated by evaporation and dried to produce a glucaric acid product containing 1.2% water (determined by Karl-Fischer titration). This material was redissolved in acetic acid and HBr to make 250 mL of a solution which was 0.2 M in HBr and contained 9.6 g of the glucaric acid product. This solution was run through a fixed bed reactor containing 2.5 g of 2.3 wt. % Pt-0.8 wt. % Rh on Davisil 635 silica at a flow rate of 50 μL/min with a concurrent hydrogen flow rate of 5 sccm at 1000 psi. The reactor has two heated zones. The first zone was a 6-inch zone heated at 110° C. and next zone was another 6 inch zone heated at 140° C.

Recovery of Composition of Matter of the Present Invention 200 mL of solution collected from the outlet of the fixed bed reactor was evaporated to dryness. Acetic acid was added (3 mL AcOH per gram crude) and the material was dissolved at 90° C. and allowed to crystallize at room temperature. Crystals were recovered by filtration and further recrystallized an additional 3 times from water using a concentration of 1 g of crystals in 5 mL of water. During the second recrystallization, the hot solution was filtered through decolorizing carbon. Finally, the crystals were dried under vacuum at 60° C. The adipic acid crystals were determined to be >99.5 wt % pure by $^1$H NMR. Mass spectrometry revealed peaks consistent with the presence the molecules depicted below, at levels <0.5 wt %.

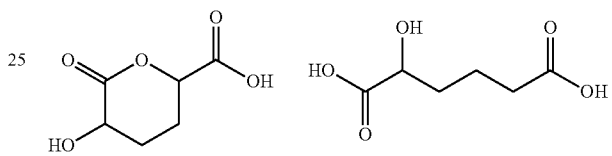

What is claimed is:

1. A composition comprising an adipic acid product of formula (1)

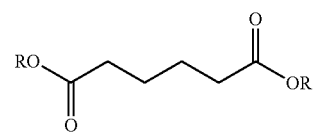

wherein R is independently a salt-forming ion, hydrogen, hydrocarbyl, or substituted hydrocarbyl, and at least two different compounds each selected from the group consisting of formula (2)

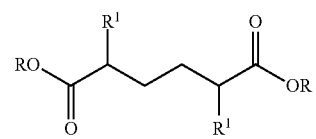

wherein R is as defined above, R¹ is H, OH, acyloxy or substituted acyloxy provided, however, at least one or R¹ is OH, and formula (3)

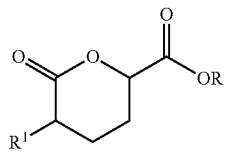

wherein R is as defined above and R¹ is H, OH, acyloxy or substituted acyloxy.

2. The composition of claim 1 comprising at least about 99 wt % adipic acid or a salt thereof and up to about 1 wt % of at least one compound of formula (2).

3. A composition comprising at least about 99 wt % adipic acid and up to about 1 wt % of at least one compound selected from the group consisting of formula (2)

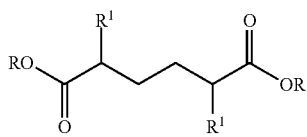

wherein R is independently a salt-forming ion, hydrogen, hydrocarbyl, or substituted hydrocarbyl, R¹ is H, OH, acyloxy or Substituted acyloxy provided, however, at least one of R¹ is OH selected and formula (3)

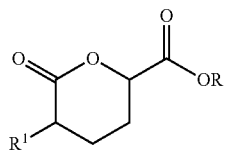

wherein R is as above defined and R³ is H, OH, acyloxy or substituted acyloxy.

4. The composition of claim 1 comprising at least about 99 wt % adipic acid and tip to about 1 wt % of at least two compounds each selected from the group consisting of formula (2) and formula (3).

5. The composition of claim 1 wherein each R of formulas (1), (2), and (3) is independently a salt-forming ion, hydrogen, hydrocarbyl containing 1 to 18 carbon atoms, or substituted hydrocarbyl containing 1 to 18 carbon atoms.

6. The composition of claim 5 wherein the hydrocarbyl containing 1 to 18 carbon atoms is selected from the group consisting of alkyl, alkylene, alkoxy, alkylamino, thioalkyl, haloalkyl, cycloalkyl, cycloalkylalkyl, heterocyclyl, N-heterocyclyl, heterocyclylalkyl, aryl, aralkyl heteroaryl, N-heteroaryl, and heteroarylalkyl.

7. The composition of claim 5 wherein the substituted hydrocarbyl containing 1 to 18 carbon atoms is selected from the group consisting of substituted alkyl and substituted cycloalkyl.

8. The composition of claim 1 wherein the salt-forming ion is selected from the group consisting of ammonium ions, alkali metal ions, and alkaline earth metal ions.

9. The composition of claim 1 wherein each R of formulas (1), (2), and (3) is independently hydrogen or a salt-forming ion selected from the group consisting of ammonium ions, alkali metal ions, and alkaline earth metal ions.

10. The composition of claim 1 wherein each R of formulas (1), (2), and (3) is independently hydrogen.

11. The composition of claim 1 wherein each $R_1$ of formulas (1), (2), and (3) is independently hydrogen or OH.

12. The composition of claim 3 wherein each R of formulas (2) and (3) is independently a salt-forming ion, hydrogen, hyrocarbyl containing 1 to 18 carbon atoms, or substituted hydrocarbyl containing 1 to 18 carbon atoms.

13. The composition of claim 12 wherein the hydrocarbyl containing 1 to 18 carbon atoms is selected from the group consisting of alkyl, alkylene, alkoxy, alkylamino, thioalkyl, haloalkyl, cycloalkyl, cycloalkylalkyl, heterocyclyl, N-heterocyclyl, heterocyclylalkyl, aryl, aralkyl heteroaryl, N-heteroaryl, and heteroarylalkyl.

14. The composition claim 12 wherein the substituted hydrocarbyl containing 1 to 18 carbon atoms is selected from the group consisting of substituted alkyl and substituted cycloalkyl.

15. The composition of claim 3 wherein the salt-forming son is selected from the group consisting of ammonium ions, alkali metal ions, and alkaline earth metal ions.

16. The composition of claim 3 wherein each R of formulas (2) and (3) is independently hydrogen or a salt-forming ion selected from the group consisting of ammonium ions, alkali metal ions, and alkaline earth metal ions.

17. The composition of claim 3 wherein each R of formula (2) and (3) is independently hydrogen.

18. The composition of claim 3 wherein each $R_1$ of formulas (2) and (3) is independently hydrogen or OH.

* * * * *

UNITED STATES PATENT AND TRADEMARK OFFICE
CERTIFICATE OF CORRECTION

PATENT NO.        : 8,669,393 B2                                      Page 1 of 1
APPLICATION NO.   : 12/966783
DATED             : March 11, 2014
INVENTOR(S)       : Thomas R. Boussie et al.

It is certified that error appears in the above-identified patent and that said Letters Patent is hereby corrected as shown below:

In the Claims:

Column 15, Claim 3, Line 33:   "Substituted" should read --substituted--.

Column 15, Claim 3, Line 46:   "$R^3$" should read --$R^1$--.

Column 15, Claim 4, Line 49:   "tip" should read --"up"--.

Column 16, Claim 11, Line 23:  "$R_1$" should read --$R^1$--.

Column 16, Claim 18, Line 48:  "$R_1$" should read --$R^1$--.

Signed and Sealed this
Twenty-third Day of September, 2014

Michelle K. Lee
*Deputy Director of the United States Patent and Trademark Office*